United States Patent [19]

Pigeon et al.

[11] 4,389,611
[45] Jun. 21, 1983

[54] APPARATUS FOR DISPLACING A SENSOR INTO A TUBE AND AUTOMATICALLY RETURNING IT

[75] Inventors: Michel Pigeon, Bures sur Yvette; Claude Viénot, Fontenzy sous Bois; Robert Saglio, Antony, all of France

[73] Assignee: Commissariate a l'Energie Atomique, France

[21] Appl. No.: 190,876

[22] Filed: Sep. 25, 1980

[30] Foreign Application Priority Data

Sep. 27, 1979 [FR] France ............................... 79 24048

[51] Int. Cl.³ ...................... G01R 33/12; G01N 27/90; B65H 49/00
[52] U.S. Cl. ...................................... 324/220; 226/49; 254/134.4; 324/226
[58] Field of Search ............................. 324/219–221, 324/207, 208, 262, 226; 254/134.4; 175/45; 226/49

[56] References Cited

U.S. PATENT DOCUMENTS 3,277,420 10/1966 Council ............................ 324/51 X
3,495,546 2/1970 Brown et al. ................ 254/134.4 X
4,087,748 5/1978 Pigeon et al. ........................ 324/220

Primary Examiner—Gerard R. Strecker
Attorney, Agent, or Firm—Thomas J. Greer, Jr.

[57] ABSTRACT

An apparatus for sending a sensor, such as an eddy current sensor, into a condenser, heat exchanger or steam generator tube. The apparatus first sends the sensor, which is attached to a cable, into the tube by means of a pressurized fluid which pushes the sensor along tube interior. At the extreme of the sensor's travel into the tube, a first ferrule attached to the rear of the cable blocks a first hydraulic passage in the apparatus. By virtue of slidable control pistons in the apparatus, this blocking cuts off the pushing pressure behind the sensor and then causes wheels to frictionally engage the cable to pull the sensor back to its starting position. At this time, another ferrule, carried near the sensor end of the cable, blocks a second hydraulic passage to thereby disengage the wheels from the cable. The cycle of (1) sensor pushed into the tube (2) sensor withdrawn from the tube, is now complete.

12 Claims, 6 Drawing Figures

APPARATUS FOR DISPLACING A SENSOR INTO A TUBE AND AUTOMATICALLY RETURNING IT

BACKGROUND OF THE INVENTION

The invention relates to an apparatus for the displacement of a sensor for the control of tubes, such as heat exchanger tubes, for example by means of eddy current sensors.

In the case of equipment such as condensers, heat exchangers and steam generators, it is necessary to be able to at all times control or inspect tubes, particularly when the primary and secondary liquids of the exchanger are incompatable or when one of the fluids has been previously irradiated which is the case, for example, in exchangers used in nuclear reactors.

In view of the large number of tubes used in such equipment, the control or inspection thereof is a long, constraining operation. It is therefore necessary to reduce to a minimum the dead times constituted by the introduction of the sensor into the tube, the starting up of the recorders, changing the tubes, etc.

The hitherto known devices for controlling tubes of equipment such as heat exchangers by means of eddy current sensors are generally pneumatic devices of the pulling—pushing—winding type, which are very heavy and are not always automatic.

BRIEF SUMMARY OF THE INVENTION

In the particular case of controlling or inspecting straight tubes of the given length, the invention relates to a displacement apparatus for a control sensor which is both portable and/or automatic, while at the same time making it possible to introduce the sensor very rapidly into the tube and then to draw it back at a regular and preferably regulatable speed.

The present invention therefore proposes an apparatus for displacing a sensor for inspecting or controlling tubes, particularly an eddy current sensor, wherein it comprises means for detecting the front and rear end positions of the sensor in the tube, a pressurized fluid source, means for the electrical displacement of the sensor which are normally disengaged and an automatic control system operated by a pressurized fluid which is sensitive to the pressurized fluid from the source and for the operation of the detection means for successively controlling the linking of the source and the tube in order to introduce the sensor into the tube, the interruption of this link when the sensor reaches its extreme front position, the engagement and operation of the electrical displacement means for removing the sensor from the tube and the disengagement and stopping of the electrical displacement means when the sensor reaches its extreme rear position.

Preferably, the electrical displacement means define a constant and regulatable sensor extraction speed.

According to another feature of the invention the automatic control system comprises a box defining a bore and a slide valve slidingly received within said bore, the box defining an inlet linked with the pressurized fluid source, a first outlet linked with the tube and a second outlet linked with the engagement means and with the means for operating the electrical displacement means, the slide valve being sensitive to the operation of the front and rear detection means so that it is moved within the bore in order to connect the inlet to one or other of the outlets.

The engagement means for the electrical displacement means can comprise at least two rollers which can frictionally engage with a cable to which the sensor is connected under the action of the pressurized fluid from the second outlet counter to elastic return means, the means for operating the electrical displacement means incorporating a manocontact (pressure contact) which is sensitive to the pressurized fluid from the second outlet, at least one of the said rollers being rotated by the electrical displacement means during their operation.

According to another secondary feature of the invention, the detection means comprise a front member and a rear member carried by a cable to which the sensor is connected, said members being able to block a front leak hole and a rear leak hole connected to the pressurized fluid source when the sensor reaches the extreme front position and the extreme rear position respectively in order to control the operation of the automatic control system. Preferably, the cable to which the sensor is connected is then received in a passage in the box, the passage defining a front portion and a rear portion which respectively receive the front member and the rear member, the front and rear leak holes issuing respectively into the front and rear portions of the passage. The box can be constructed so as to have two articulated parts, whose joining plane passes through the axis of the passage making it possible to place the cable and the sensor within the apparatus. Preferably, the electrical displacement means are then located in one of these parts and the automatic control system in the other part.

According to a secondary feature of the invention, the front and rear members in each case comprise a portion fixed to the cable to which is connected the sensor, a portion able to seal the corresponding leak hole and damping means located between the said portions.

According to yet another feature of the invention, the automatic control system also has a first piston slidingly received in the bore and defining with the box wall a front chamber linked with the rear leak hole in such a way that the sealing of the latter by the rear member controls the displacement of the first piston and the slide valve so as to interrupt the connection between the inlet and the first outlet and produce a connection between the inlet and the second outlet.

According to yet another feature of the invention, the automatic control system also has a second piston slidingly received in the second bore and defining with the box wall a rear chamber connected to the inlet and the front leak hole, the box also defining a second inlet connected to the engagement means and the means for operating the electrical displacement means and an exhaust port connected to the atmosphere, the second piston being moved by elastic means towards a position in which the connection between the second inlet and the exhaust port is interrupted and the sealing of the front leak hole by the front member controls the displacement of the second piston counter to the elastic means so as to establish the said connection.

BRIEF DESCRIPTION OF THE DRAWINGS

The invention is described in greater detail hereinafter relative to non-limitative embodiments and the attached drawings, wherein.

DETAILED DESCRIPTION OF THE PREFERRED EMBODIMENTS

Figure 1:
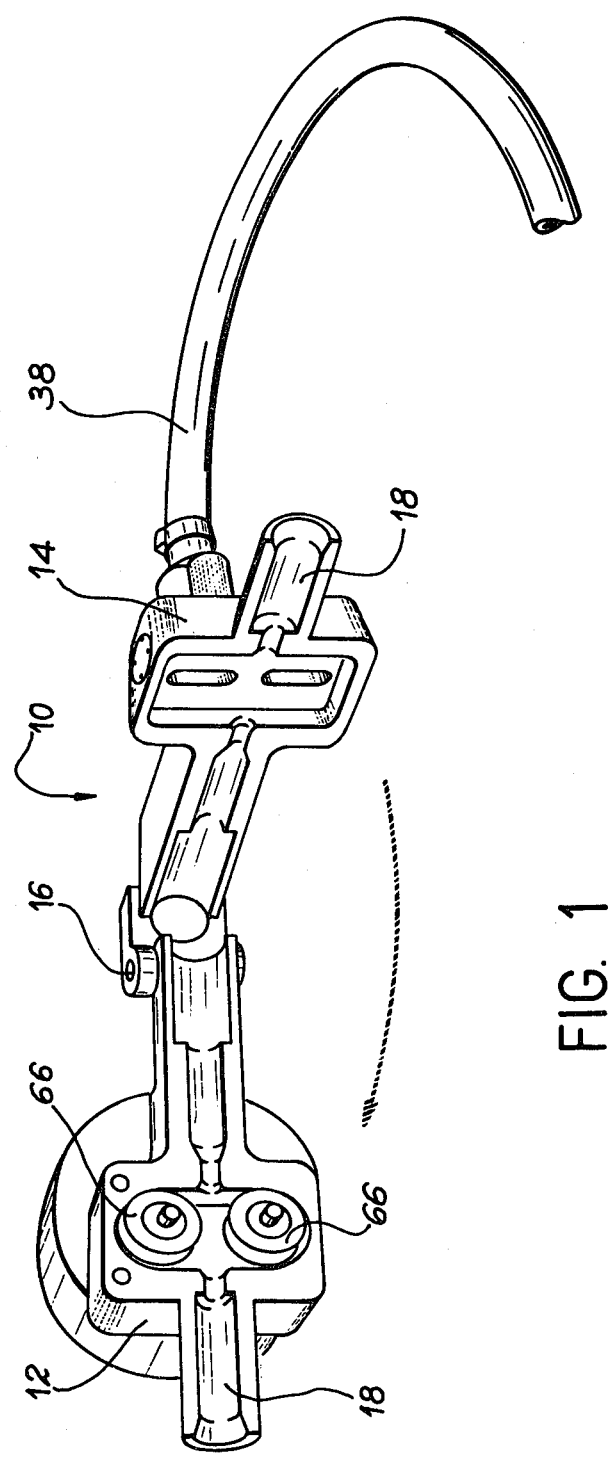
FIG. 1 a perspective view of a portable displacement apparatus in accordance with the invention.

As is illustrated by FIG. 1, the displacement apparatus according to the invention, designated in general manner by the reference numeral 10, comprises a two-part box or case 12 and 14 articulated about a pin 16. The joining plane of parts 12 and 14 of the box passes through the axis of a passage 18 for receiving a cable 20 to which is connected a sensor 22 for controlling or inspecting the tubes, such as an eddy current sensor and as illustrated in particular in FIG. 2. The displacement apparatus 10 according to the invention is designed in such a way as to introduce sensor 22 as rapidly as possible therefore into a straight tube of given length which it is necessary to inspect in per se known manner by means of sensor 22 during the return of the latter towards the apparatus and which preferably takes place at a regular and regulatable speed. The tubes to be automatically inspected in this way are generally contained in equipment having a large number of such tubes, such as condensers, steam generators and heat exchangers.

Figure 3:
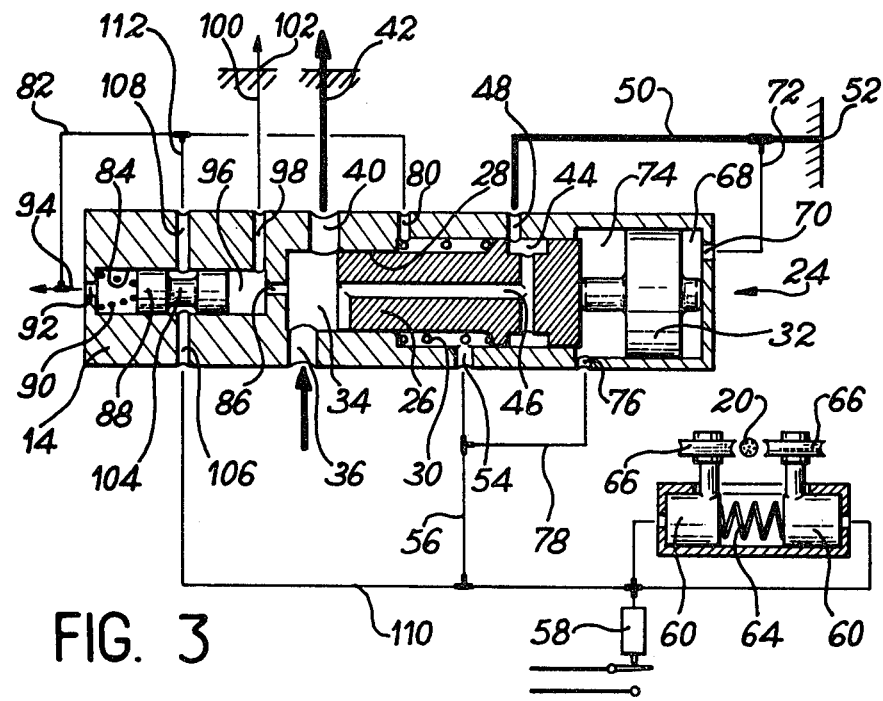
FIGS. 3, 4, 5 and 6 longitudinal sectional views of the pressurized fluid automatically controlled system of the displacement apparatus shown in FIGS. a and 2 diagrammatically illustrating the different operating phases thereof.

According to the invention and as illustrated more particularly in FIG. 3, the displacement device 10 comprises a pressurized fluid automatic control system designated in general manner by reference numeral 24 and located in part 14 of the box. System 24 comprises a slide valve 26 slidingly received in a stepped bore 28 formed in part 14 of the box. Slide valve 26 and bore 28 have a larger diameter portion and a smaller diameter portion which, between them, define shoulders on which can bear a spring 30 which displaces slide valve 26 to the right in FIG. 3 so as to abut against a piston 32 located between the right-hand end of slide valve 26 and the bottom of bore 28.

Figure 2:
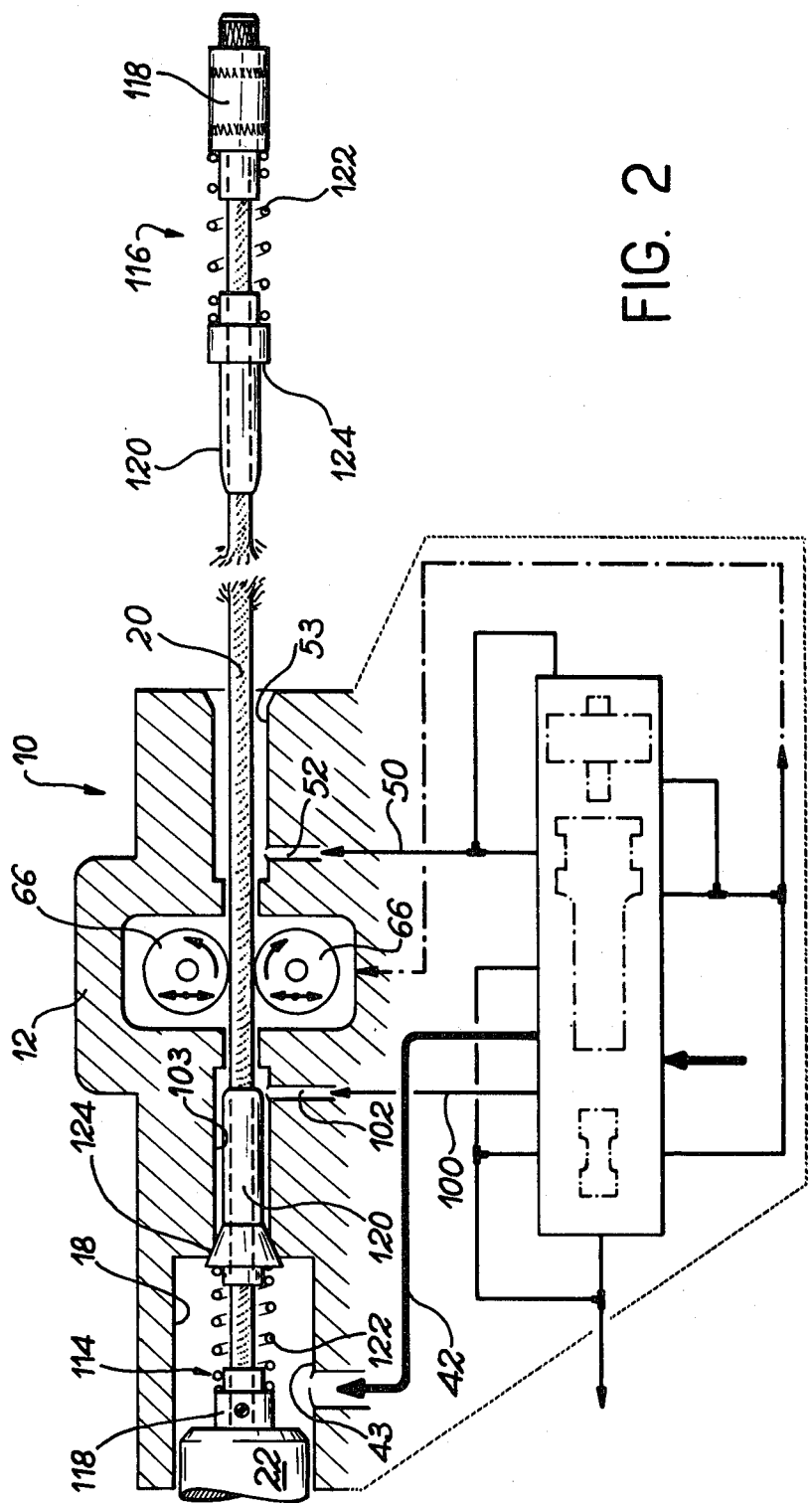
FIG. 2 a longitudinal sectional view of the apparatus of FIG. 1 which more particularly shows the means for detecting the extreme front and rear positions of the sensor in the tube carried by the cable to which the sensor is connected.

When the slide valve 26 is in its inoperative position shown in FIG. 3, an inlet chamber 34 between the left-hand end of slide valve 26 and part 14 of the box is connected to a pressurized fluid source (diagrammatically indicated by an arrow) by an inlet 36 to which is connected a flexible tube 38 shown in FIG. 1. Chamber 34 is also connected by an outlet 40 and via a passage diagrammatically indicated at 42 to a larger diameter portion 43 of passage 18 for receiving sensor 22 and as illustrated in FIG. 2. Outlet 40 is slightly displaced to the right with respect to passage 36, as illustrated more particularly in FIG. 3, in such a way that it is blocked by slide valve 26 when the latter moves to the left counter to spring 30 and before the valve abuts against the left-hand end of bore 28. Inlet 36 is permanently connected to an annular chamber 44 defined in the larger diameter portion of slide valve 26 by a longitudinal passage 46 made therein. As illustrated in FIG. 3, the annular chamber 44 is connected by an outlet 48 and a passage 50 with a rear leak hole 52 issuing into a portion 53 of passage 18 positioned in the vicinity of the end of the latter which is opposite to sensor 22, when slide valve 26 is in the inoperative position.

Figure 5:
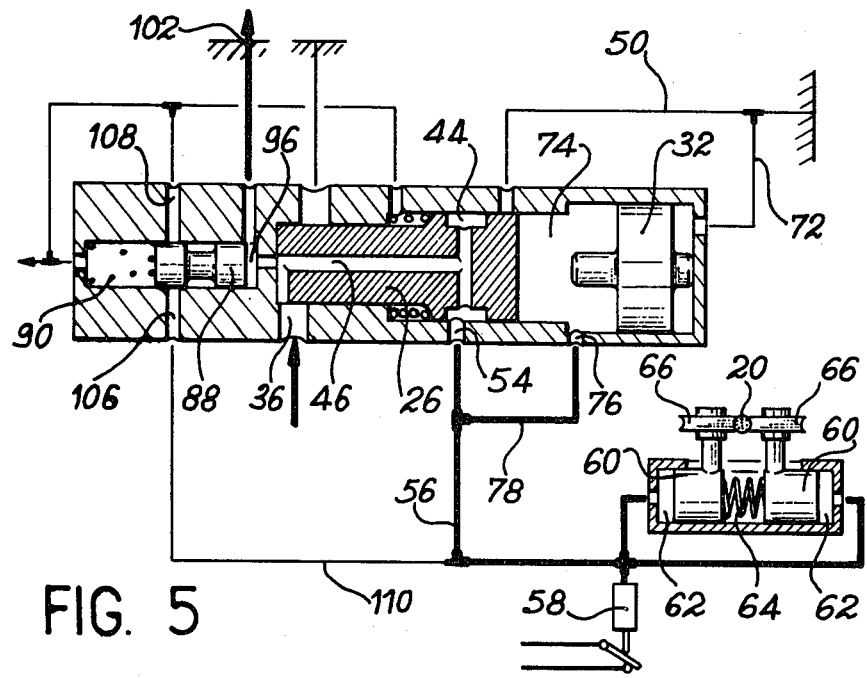

Conversely and as is more particularly illustrated in FIG. 5, when slide valve 26 is moved into its extreme left position counter to spring 30, annular chamber 44 is connected via a second outlet 54 and a passage 56 with a manocontact or pressure contact 58 controlling the operation of a not shown electric drive motor and with two chambers 62 controlling the displacement of two pistons 60 towards one another and counter to a spring 64 positioned between piston 60, so that it brings two drive rollers 66 into frictional engagement with cable 60. The electric drive motor, whose operation is controlled by manocontact 58, rotates the roller 66, which thus frictionally displace the cable 20 in the direction corresponding to the return of sensor 22 to apparatus 10, as will be shown hereinafter.

For reasons which will become apparent hereinafter, a front chamber 68 defined between piston 32 and the bottom of bore 28 is connected by an orifice 70 and a passage 72 with the leak passage 50, and a chamber 74 defined between piston 32 and slide valve 26 is connected by an orifice 76 and a passage 78 with passage 56. In addition, the chamber containing spring 30 is permanently connected to the atmosphere by an orifice 80 and a passage 82.

As is more particularly illustrated in FIG. 3, a second bore 84 is made in case 14 in the extension of bore 28 and on the side opposite to piston 32. Bore 84 slidingly receives a second piston 88 which is moved to the right with respect to FIG. 3 by a spring 90 positioned between piston 88 and the end of bore 84 opposite to bore 28. Like the annular chamber receiving spring 30, the chamber which receives spring 90 is connected to the atmosphere by an orifice 92 and a passage 94. Moreover, a rear chamber 96 defined between piston 88 and the other end of bore 84 is connected to the inlet chamber 34 by a passage 86 and has an outlet 98 which is connected by a passage 100 with a front leak hole 102 issuing into a portion 103 of passage 18 retracted from the large diameter portion 43 for receiving sensor 22. The central portion of piston 88 has a groove 104 for linking the second inlet 106 with an exhaust port 108 when the pressure in chamber 96 displaces piston 88 counter to the tension exerted by spring 90. Inlet 106 is connected by a passage 110 with passage 56 and port 108 is connected by a passage 112 with passage 82, in such a way that manocontact 58 and chambers 62 are connected to the atmosphere when piston 88 occupies this position.

As is more particularly illustrated in FIG. 2, the front leak hole 102 and rear hole 52 can be sealed respectively by a front member 114 and a rear member 116. Each of the members 114, 116 has a collar 118 rigidly fixed to cable 20 and a ferrule 120 able to slide with respect to cable 20 and connected to collar 118 by a damping spring 122. The ferrules 120 of each of the members 114 and 116 are positioned on the side of the case of the displacement apparatus 10 relative to collar 118, so as to penetrate portions 103 and 53 of passage 18 in which are respectively made orifices 102 and 52 and abut by a shoulder 124 against the corresponding ends of the said portions when sensor 22 occupies its extreme front position or its extreme rear position with respect to the tube to be inspected.

The apparatus described hereinbefore to FIGS. 1 to 6 functions in the following manner. When the displacement apparatus according to the invention is in the inoperative position, sensor 22 is located in portion 43 of passage 18 and the ferrule 120 of front member 114 is located in portion 103 of passage 18 and abuts by its shoulder 124, as illustrated in FIG. 2. The front leak hole 102 is therefore closed, whilst the rear leak hole 52 is open. Moreover, the various elements of the pressurized fluid automatic control system 24 then occupy the position shown in FIG. 3. Moreover, pistons 60 are moved away from one another by spring 64, in such a way that rollers 66 are kept remote from cable 20 and manocontact 58 is opened. Orifices 54 and 106 are respectively linked with orifices 80 and 108, i.e. with atmosphere via passages 82 and 112.

Figure 4:
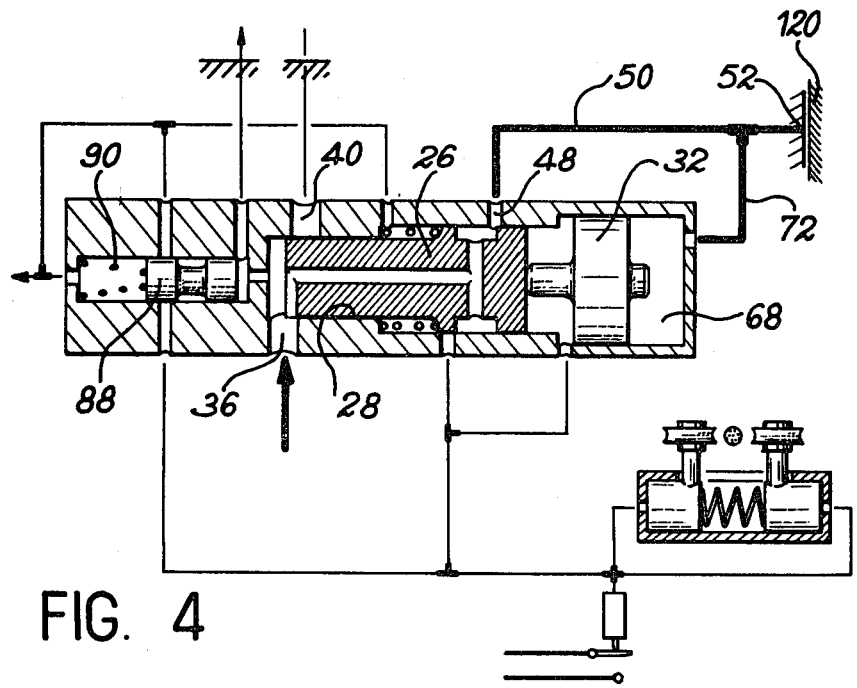

When it is desired to control or inspect a straight tube of given length in an apparatus such as a condenser, heat exchanger or steam generator, the left end (FIG. 2) of passage 18 is connected to said tube, for example by making it directly face the latter. Pressurized fluid from the not shown source is then introduced into chamber 34 via flexible pipe 38 and inlet 36. This fluid is directly admitted into portion 43 of passage 18 by outlet 40 and passage 42 in such a way that sensor 22 and cable 20, together with members 114 and 116 which are associated therewith are moved to the left, with reference to FIG. 2 within the tube to be inspected (not shown). The front leak hole 102 is immediately opened and pressure drops in chamber 96 in such a way that piston 88 is moved to the right under the action of spring 90. This has the effect of interrupting the connection between orifices 106 and 108, as illustrated in FIG. 4. The pressurized fluid introduced into chamber 34 is also passed to the rear leak hole 52 via passage 46, annular chamber 44, orifice 58 and passage 50 and to front leak hole 102 via passage 86, chamber 96, orifice 98 and passage 100. As the ferrules 120 are still both remote from the corresponding portions 53 and 103 of passage 18, the pressurized fluid which escapes via orifices 52 and 102 passes to atmosphere and has no effect on the operation of the system 24. Therefore, as sensor 22 is introduced into the tube to be inspected directly under the action of the pressurized fluid, this operation takes place very rapidly.

When the sensor 22 reaches the end of the tube to be inspected, the ferrule 120 of rear member 116 penetrates the portion 53 of passage 18 and its end is engaged by its shoulder 124 in such a way that the rear leak hole 52 is no longer connected to atmosphere. Therefore, the pressure in passages 50 and 72 increases rapidly and piston 52 and slide valve 26 are moved to the left under the action of the pressure in chamber 68 so as to seal the outlet 40, as illustrated in FIG. 4. Thus, the connection between the not shown pressurized fluid source and, via portion 43 of passage 18, the tube to be inspected is interrupted. Thus, the outward movement of sensor 22 in the tube inspection is at an end. It should be noted that the construction of member 116 in two portions 118 and 120 connected by a spring 122 makes it possible to damp the impact caused by the sudden return of the sensor by compressing spring 122 between collar 118 and ferrule 120.

On continuing their movement to the left resulting from the sealing of the rear leak hole 52, piston 32 and slide valve 26 abut against the left-hand end of bore 28. In this position and as illustrated in FIG. 5, annular chamber 44 is no longer connected to orifice 48 and is instead connected to its orifice 54. Thus, the pressurized fluid introduced by inlet 36 is no longer introduced into chamber 68 via passages 50 and 72, while the pressurized fluid is simultaneously connected to manocontact 58 and chambers 62 via passage 56 and to chamber 74 via passage 78 and orifice 76. This simultaneously brings about the closing of the electric circuit supplying the electric motor driving rollers 66, the frictional contact between the latter and cable 20 and the return of piston 32 to its inoperative position as illustrated in FIG. 5. The pressurization of passages 78 and 56 is possible due to the fact that piston 88 is displaced to the right under the action of spring 90, so that the connection between orifices 106 and 108 is interrupted and passage 110 is no longer connected to atmosphere. This is due to the fact that the front leak hole 102 is not blocked by ferrule 120 of member 114, so that chambers 96 is connected to atmosphere. Thus, sensor 22 is brought back towards the displacement apparatus 10 by the not shown electric motor acting on roller 66 at a constant, regulatable speed between, for example, 0.05 and 0.5 m/s.

Figure 6:
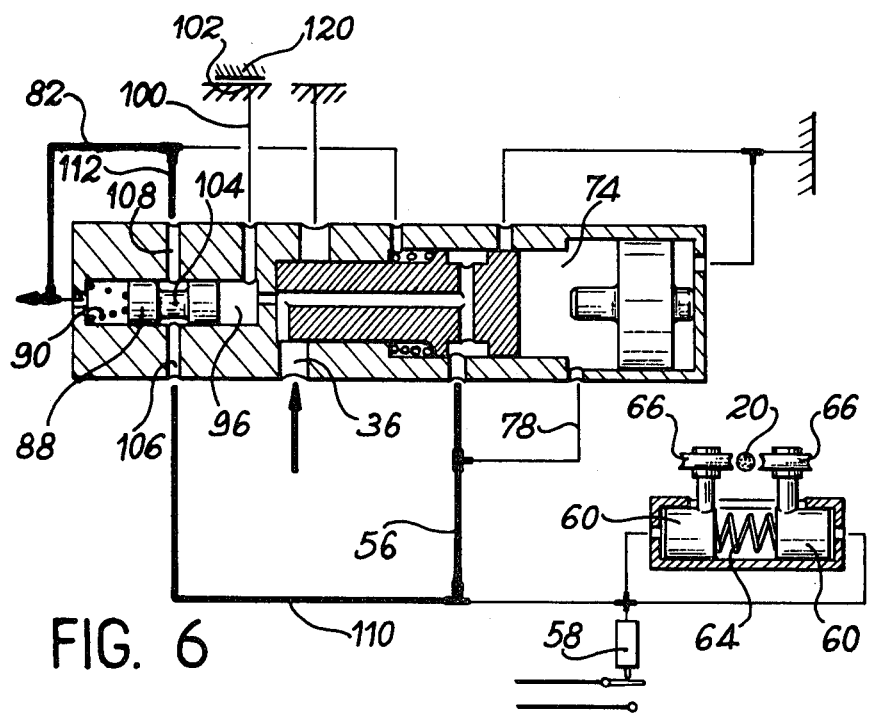

When sensor 22 returns to portion 43 of passage 18 in the displacement apparatus 10 under the action of the displacement force exerted by rollers 66 on cable 20 by the not shown electric motor and at a constant, regulatable speed, ferrule 120 of front member 114 enters portion 103 of passage 18 in such a way that shoulder 124 engages on the end of portion 103, as illustrated in FIG. 2. The front leak hole 102 is then blocked, so that the pressure in passage 100 and chamber 96 increases. Piston 88 is then moved to the left counter to spring 90, as illustrated in FIG. 6. Groove 104 on piston 80 then faces passages 106 and 108 in such a way that chamber 62, manocontact 58 and chamber 74 are connected to atmosphere. The operation of rollers 66 by the electric motor is interrupted and the rollers are again moved away from cable 20 under the action of spring 64. As member 114 is formed in three parts, it is possible for left spring 122 to dampen the impact caused by the penetration of ferrule 120 into portion 103 of passage 18.

As soon as the connection between the pressurized fluid source and inlet 36 of the system 24 is interrupted the slide valve 26 resumed the position shown in FIG. 3, so that once again a tube can be inspected by connecting the free end of portion 43 of passage 18 to the said tube.

It can be gathered from what has been stated hereinbefore that the design and construction of the sensor displacement apparatus according to the invention are particularly simple and as a result the apparatus can be in the form of a portable gun with a single control means, whereby it can successively be made to face each of the tubes in the equipment to be inspected. All the movements of the sensor within the tube are brought about by operating a single control means associated with the not shown pressurized fluid source making it possible to link the pressurized fluid by flexible tube 38 with inlet 36 of automatic control system 24. The latter then automatically and successively controls the rapid introduction of the probe into the tube by pressurized fluid, the interruption of the pressurized fluid link between the source and the tube to be controlled when the sensor reaches its extreme front position, the engagement and operation of the displacement means at constant, regulatable speed constituted by the not shown electric drive motor and rollers 66, so as to inspect the tube by moving back the sensor at the desired constant speed and finally the disengagement and stoppage of the electric displacement means when the sensor reaches its extreme rear position shown in FIG. 2.

What is claimed is:

1. An apparatus for displacing and controlling a sensor for tubes, particularly an eddy current sensor, comprising, a cable to which said sensor is connected, means for engaging and displacing said cable, front and rear detection means for detecting front and rear extreme positions of the sensor in the tube, a pressurized fluid source, and an automatic control system operated by a pressurized fluid, said control system comprising at least one box defining at least one bore therewithin, and at least one slide valve slidingly received within said bore, said box having an inlet which communicates with said pressurized fluid source and at least one outlet which is adapted to communicate with the tube to be inspected, the outlet located behind said sensor, and means for actuating said cable engaging and displacing means, said actuating means being sensitive to the position of the slide valve in said bore, said slide valve being sensitive to the operation of said front and rear detection means for sliding within said bore, in order either to communicate the inlet with the outlet, or to actuate said cable engaging and displacing means, respectively.

2. An apparatus according to claim 1, wherein the cable engaging and displacing means effects a constant and regulatable sensor removal speed.

3. An apparatus according to claim 1, wherein said box includes a second outlet which communicates with a manocontact for controlling said cable engaging and displacing means.

4. An apparatus according to claim 3, wherein said cable engaging and displacing means acts on said cable through clutch means normally disengaged from said cable.

5. An apparatus according to claim 4, wherein said clutch means includes at least two rollers which frictionally engage said cable under the action of said pressurized fluid supplied from said second outlet, said rollers being normally urged not to engage the cable.

6. An apparatus according to claim 1, wherein the detection member comprise a front member and a rear member carried by said cable, said members blocking a front leak hole and a rear leak hole communicating the pressurized fluid source when the sensor reaches the front position and the rear position, respectively, in order to control operation of said automatic control system.

7. An apparatus according to claim 6, wherein said cable is received in a passage in said box, said passage defining a front portion and a rear portion, which portions respectively receive the cable front member and the cable rear member, said front and rear leak holes communicating with, respectively, the front and rear portions of said passage.

8. An apparatus according to claim 7, wherein the box is constructed in the form of two articulated parts, whose joining plane passes through the axis of said cable passage.

9. An apparatus according to claim 8, wherein said cable engaging and displacement means are located in one of the said parts, while said automatic control system is located in the other part.

10. An apparatus according to claim 6, wherein the cable front and rear members each comprise a ferrule fixed to said cable, a portion of each ferrule sealing the corresponding leak holes located between the said portions.

11. An apparatus according to claim 6, wherein said automatic control system also has a first piston slidingly received in the bore and defining with a wall of said box a front chamber communicating with the rear leak hole in such a way that the sealing of the latter by the rear member controls the displacement of the first piston and the slide valve so as to interrupt the communication between the inlet and the first outlet and produce a communication between the inlet and the second outlet.

12. An apparatus according to claim 11, wherein the automatic control system also has a second piston slidingly received in the second bore and defining with a wall of said box a rear chamber communicating with the inlet and the front leak hole, said box also defining an exhaust port communicating with the atmosphere, the second piston being moved by elastic means towards a position in which the communication between the second inlet and the exhaust port is interrupted and the sealing of the front leak hole by the front member controls the displacement of the second piston counter to the elastic means so as to establish the said communication.

* * * * *